United States Patent [19]

Rovati et al.

[11] Patent Number: 4,576,951

[45] Date of Patent: Mar. 18, 1986

[54] PROGLUMIDE, PHARMACEUTICAL PREPARATIONS AND COMPOSITIONS INCLUDING IT FOR USE IN HUMAN PAIN RELIEF

[75] Inventors: Luigi Rovati; Francesco Makovec; Paolo Senin; Pierluigi Casula, all of Monza, Italy

[73] Assignee: Rotta Research Laboratorium S.p.A., Milan, Italy

[21] Appl. No.: 680,004

[22] Filed: Dec. 10, 1984

[30] Foreign Application Priority Data

Dec. 12, 1983 [IT] Italy ................................ 68288 A/83

[51] Int. Cl.[4] ..................... A61K 31/44; A61K 31/195
[52] U.S. Cl. ..................................... 514/282; 514/563
[58] Field of Search ................. 424/260; 514/282, 563

[56] References Cited

PUBLICATIONS

Chem. Abst. 101-65877Q (1984) & 100-203518F (1984).

Primary Examiner—Stanley J. Friedman
Attorney, Agent, or Firm—Saidman, Sterne, Kessler & Goldstein

[57] ABSTRACT

The subject of the invention is a new use of D,L-4-benzamido-N,N-dipropyl-glutaramic acid (proglumide) in human pain relief. According to the invention proglumide is used both alone, at dosages of from 0.5 to 30 mg/kg of body weight, and in association with analgesic-narcotic drugs, it being able to potentiate the analgesic activity of these drugs.

8 Claims, 2 Drawing Figures

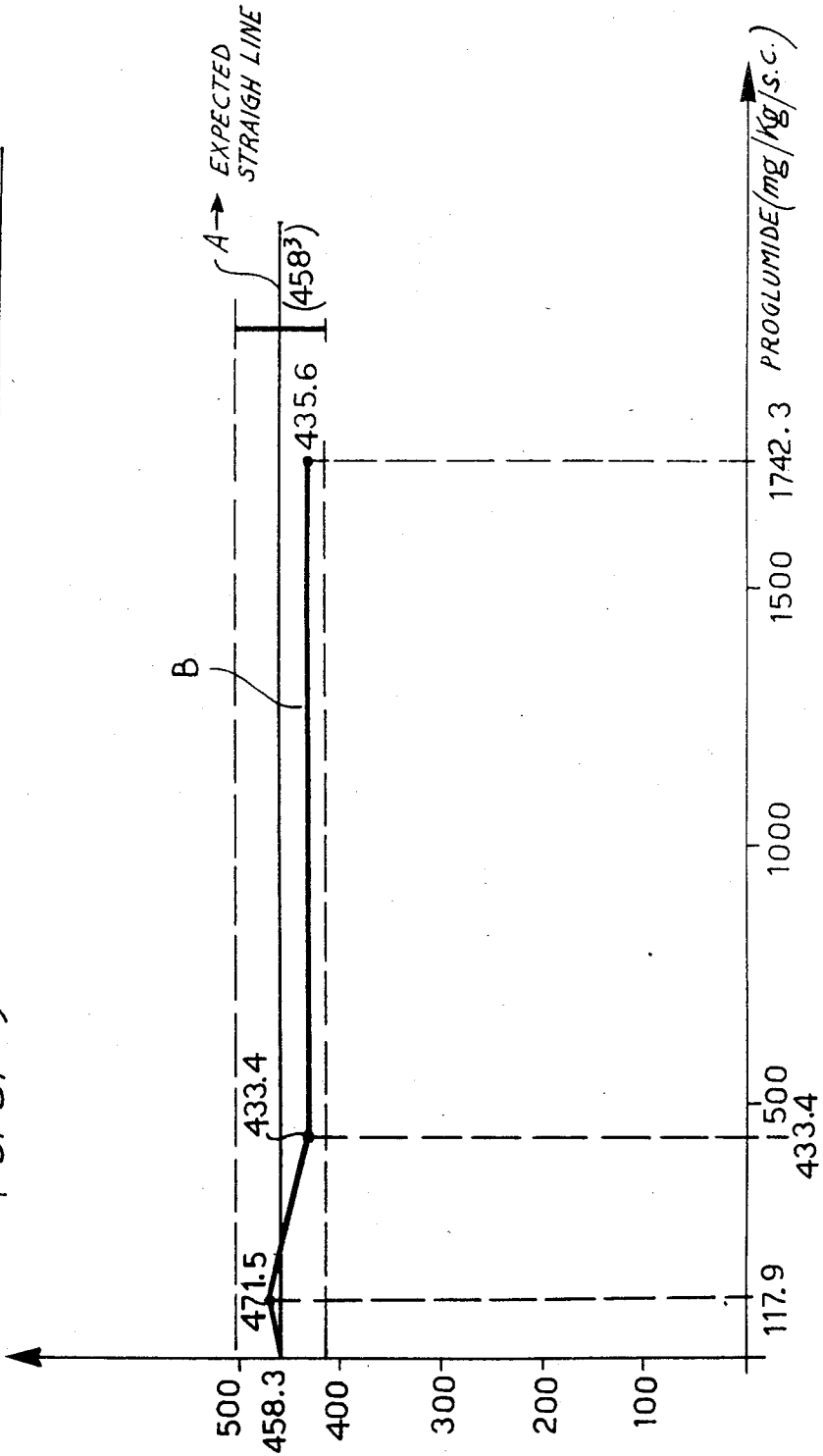
FIG. 1  ACUTE TOXICITY IN RATS s.c.

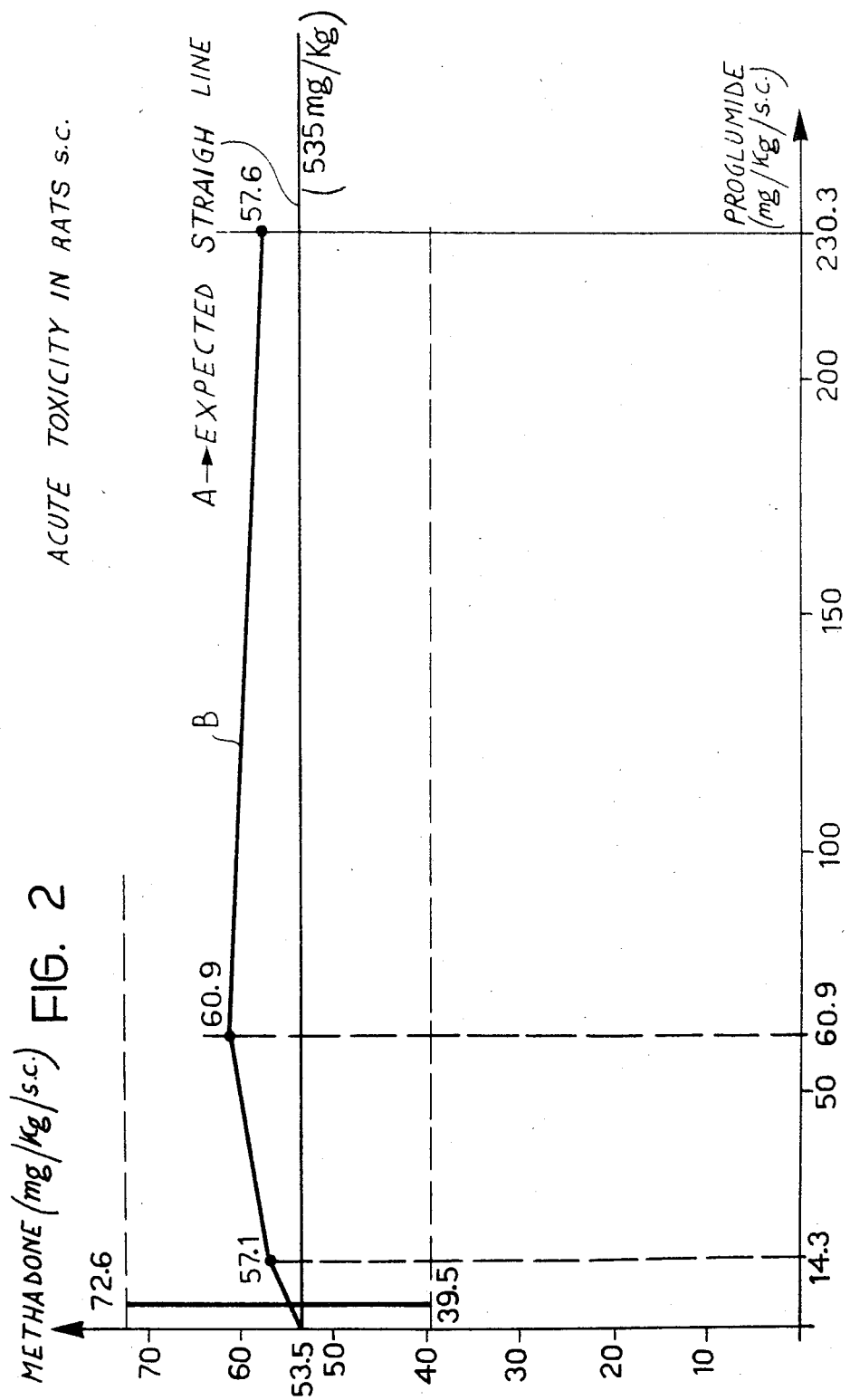

PROGLUMIDE, PHARMACEUTICAL PREPARATIONS AND COMPOSITIONS INCLUDING IT FOR USE IN HUMAN PAIN RELIEF

The subject of the present invention is a new therapeutic use of D,L-4-benzamido-N, N-dipropylglutaramic acid (proglumide) and its pharmaceutically acceptable salts for use either alone or in association with analgesic-narcotic drugs in the treatment of pain of any etiology or intensity.

The Applicants have found that the said drug, already widely used in the treatment of gastric ulcers (see for example Merck Index No. 7680), page 1120 (10th Ed. 1983) in fact has a therapeutic activity which is as unexpected as it is extremely interesting, that is, that of potentiating the analgesic activity of morphine and opiate drugs chemically related thereto.

The potentiation induced by proglumide allows the dosage of these narcotic drugs to be reduced considerably, thus reducing the whole group of well known, undesirable side effects, without also reducing the therapeutic effectiveness.

Hence the association of proglumide with opiate drugs enables a pharmaceutical composition to be made available for treatment which has the following therapeutic characteristics.

(a) It potentiates the analgesic activity of morphine and related drugs As already explained above this allows the therapeutic doses of the opiate drugs to be reduced considerably, thus considerably increasing the therapeutic indices thereof.

(b) It re-establishes the analgesic activity of opiate drugs when their pharmaceutical effect has fallen off, this being linked to the well known tolerance phenomenon, without their dosage having to be increased.

(c) It makes possible the gradual de-toxication of patients who have become addicted as a result of the prolonged use of opiate drugs.

The therapeutic novelty of this new pharmaceutical composition is based on the unexpected capacity of proglumide to potentiate the activity of morphine and related drugs by a mechanism which is very complex and which is at present only partly clarified.

This ability to potentiate the analgesic activity of narcotics may, in fact, be related to the capacity of proglumide to block the activity of cerebral enzymes responsible for the hydrolytic degradation of enkephalins, endogenous physiological peptides with strong analgesic activities. This could give the enkephalins a longer half-life and, thus, a greater activity.

In accordance with the above, the invention provides pharmaceutical compositions including proglumide or its pharmaceutically acceptable salts as the active principle for use in human pain relief.

A further subject of the present invention is constituted by pharmaceutical compositions including proglumide or its pharmaceutically acceptable salts and analgesic-narcotic drugs such as morphine or other analgesic-narcotic derivatives. Morphine-like drugs with analgesic-narcotic activities used in association with proglumide may, by way of non-limiting example, be morphine and its derivatives such as codeine and oxycodone, derivatives of morphinan such as levorphanol, derivatives of benzomorphan such as pentozocine, derivatives of 4-phenyl-piperidine such as meperidine, and derivatives of diphenyl propylamine, such as methadone and dextropropoxyphene. The drugs mentioned above may be used in the form of the free base or as the salt of a pharmaceutically-acceptable acid, for example, in the form of the hydrochloride, sulphate or phosphate.

Typically proglumide is administered to the patient at a rate of 0.5 to 30 mg/kg of body weight.

When proglumide is administered in association with analgesic-narcotic drugs, pharmaceutical compositions incorporating it have a ratio by weight of the proglumide to the analgesic-narcotic drug which is typically between 200 and 1. The new pharmaceutical compositions may be prepared by the addition to the pharmacologically-active ingredients of inactive ingredients, such as excipients, binders, flavourings, dispersants, preservatives, colouring agents, humectants, commonly used in the pharmaceutical industry. The pharmaceutical preparations may be prepared in the form of tablets, coated tablets, capsules, dragees or in the form of solutions, suspensions, emulsions for oral use or solutions which can be injected for parenteral use or as suppositories for rectal use.

Preparations for administration by the oral, parenteral or rectal routes contain quantities of proglumide of from 10 to 1500 mg of substance per unit dose, preferably 200–400 mg for the oral and rectal routes and 200–800 mg for the parenteral route and variable quantities of the analgesic-narcotic drugs depending on their relative analgesic power.

In general it is possible to reduce the daily therapeutic dosage of all these drugs from 1 to 5 times with respect to treatment with the analgesic drug alone.

A further subject of the present invention is a pharmaceutical product including proglumide or one of its pharmaceutically acceptable salts and an analgesic-narcotic agent, in the form of a combined preparation for simultaneous, separate or sequential use in human pain relief.

The preparation of different compositions in accordance with the present invention is described below, purely by way of non-limiting example.

EXAMPLE 1

Composition and preparation of a tablet containing proglumide and methadone hydrochloride Composition of a tablet

| | |
|---|---|
| Proglumide | 400 mg |
| Methadone | 5 mg |
| Lactose | 50 mg |
| Starch | 100 mg |
| Talc | 5 mg |
| Magnesium stearate | 2 mg |
| Silicon dioxide | 3 mg |

Preparation for 10,000 tablets 4000 g of proglumide are mixed with 500 g of lactose and 700 g of starch. This mixture is taken up in 300 g of starch cooked with water. The mass is ground while wet, passed through a 15 mesh sieve, dried, passed through a 20 mesh sieve and mixed with 50 g of methadone, 50 g of talc, 20 g of magnesium stearate and 30 g of silicon dioxide.

The homogeneous mixture is compressed in a rotary compressor and, with the use of 11 mm diameter punches, about 10,000 tablets of 565 mg are obtained.

By the same method it is possible to make tablets containing from 10 to 100 mg of proglumide instead of 400 mg of proglumide and from 2 to 20 mg of methadone, from 20 to 100 mg of dextropropoxyphene, from 20 to 100 mg of meperidine or from 10 to 50 mg of pentazocine instead of 5 mg of methadone.

EXAMPLE 2

Composition and preparation of a solution containing proglumide and morphine for injection Composition of a phial containing proglumide and morphine

| Proglumide sodium salt | 426.3 mg |
|---|---|
| Morphine hydrochloride | 10 mg |
| Sodium hydroxide | 1.25 mg |
| Citric acid monohydrate | 6.5 mg |
| Triethanolamine | 9.3 mg |
| Water for injectable prep. QS | 3 ml |

Preparation of 10,000 vials 15 liters of water suitable for injectable solutions and 93 g of triethanolamine are placed in a neutral glass reactor under agitation. 4263 g of sodium proglumide are added to the solution and agitated until a clear solution is obtained.

To one side, morphine hydrochloride is dissolved in 1 liter of water containing 65 g of citric acid monohydrate and 12.5 g of sodium hydroxide; the clear solution obtained is added to the preceding solution.

The resulting solution is brought to a volume of 30 liters by the addition of water for injectable preparations and filtered under pressure in an inert gas through a filter membrane (0.45 micron porosity) into small, sterile, inert glass bottles. It is then put in 3.3 ml vials and sterilised at 120° C. for 20 minutes.

By the same method it is possible to make injectable solutions containing, in a volume suitable for human treatment, from 10 to 1000 mg of proglumide instead of 400 mg of proglumide (equal to 426.3 mg of proglumide sodium salt), and from 1 to 20 mg of morphine hydrochloride, from 1 to 20 mg of methadone hydrochloride, from 10 to 1000 mg of dextropropoxyphene hydrochloride, from 10 to 50 mg of meperidine hydrochloride and from 10 to 50 mg of pentazocine hydrochloride instead of 10 mg of morphine hydrochloride.

EXAMPLE 3

Composition and preparation of an oral solution (syrup) containing proglumide and methadone hydrochloride Composition for 100 ml of syrup

| Proglumide | 2 g |
|---|---|
| Methadone hydrochloride | 0.02 g |
| Sodium hydroxide drops | 0.24 g |
| Essence | 0.05 g |
| 70% Sorbitol | 65 g |
| 95% Ethyl Alcohol | 5 g |
| Distilled water QS | 100 ml |

Preparation of 10 liters of syrup 24 g of sodium hydroxide are dissolved in about 2 liters of distilled water in a glass flask. 200 g of proglumide are added to it under agitation. When the whole has formed a solution, 2 g of methadone hydrochloride, 500 g of ethanol, 6500 g of sorbitol, 5 g of essence are then added. This is brought up to volume with distilled water. It is filtered through a bell filter and bottled. By the same method, oral solutions can be obtained which contain from 0.2 g to 4 g of proglumide/100 ml instead of 2 g of proglumide/100 ml and from 5 mg to 50 mg/100 ml of methadone hydrochloride or from 30 mg to 500 mg/100 ml of codeine hydrochloride or meperidine hydrochloride respectively instead of 20 mg/100 ml of methadone hydrochloride.

EXAMPLE 4

Composition and preparation of a suppository containing proglumide and dextropropoxyphene Composition of a suppository

| Proglumide | 300 mg |
|---|---|
| Dextropropoxyphene hydrochloride | 50 mg |
| Mixture of mono, di- and triglycerides of saturated fatty acids | 1600 mg |

Preparation of 10,000 suppositories 16 kg of the mass are melted at 45° C. and 3 kg of proglumide and 0.5 kg of dextropropoxyphene are added in small portions. When a homogeneous fluid mass has been obtained this is injected at 37°–40° C. into pre-prepared 2 ml PVC sacks in the desired quantity (1.95 g). After cooling, the sacks are closed with aluminum strips.

The same method can be used to make suppositories containing from 50 to 600 mg of proglumide instead of 300 mg of proglumide and from 10 to 100 mg of dextropropoxyphene or from 5 to 50 mg of codeine or pentazocine hydrochloride respectively instead of 50 mg of dextropropoxyphene hydrochloride.

The analgesic activity shown by the new pharmaceutical compositions which are the subject of the present invention will now be illustrated by a series of pharmacological tests arranged to demonstrate both the potentiation of the analgesic activity of opiate drugs shown by proglumide and the mechanism by which this potentiation is achieved.

EXPERIMENT 1

Increase in the analgesic effect of analgesic-narcotic drugs induced by proglumide in the Tail Flick Test on rats The method is that described by Harris et al. (J. Pharmcol. Exp. Ther. 143 (1964) 141–148).

Male rats are used which have a weight of about 150–200 g and which have not been fasting. A point is chosen on the tail and this is irradiated by a heat source (75° C.) and the time (in seconds) for which the animal remains without moving its tail is measured.

A maximum period of time under the heat source of 8 seconds is chosen after which the animal is, in any case, removed in order to avoid tissue damage. The measurement is effected before (controls) and after treatment with the drugs. The administration of proglumide is effected by i.p. 10 minutes and immediately before administration of the analgesic drug (for example morphine and dextropropoxyphene). The percentage variation is calculated for each individual animal by the following formula:

$$\% \text{ variation} = \frac{\text{pain thresold (sec)} - \text{control thresold (sec)}}{8 \text{ (sec)} - \text{control thresold (sec)}} \times 100$$

(time measurements are in seconds)

The measurements are carried out 10, 20, 30, 45, 60 and 90 minutes after treatment with the analgesics.

The results obtained are given in Table 1 which records the groups treated and the doses administered, the average percentage variation (calculated on groups of five animals) in the latency of the pain sensation, the average values calculated in the period 1–90 minutes (±S.E.) and the potency ratio of the control drugs and the respective different pharmaceutical compositions.

The animals are placed on a metal plate which is on the bottom of a transparent cylinder heated to $55°\pm1°$ C. by an azeotropic boiling mixture (1:1 acetone-ethyl formate). The time which passes between the moment at which the animal is placed on the hot plate and the moment at which it licks its feet or tries to jump out of the cylinder is defined as the reaction time. The control reaction time is measured 10 and 5 minutes before the administration of the drugs and 10, 20, 30, 45, 60, 90 minutes afterwards. The animals are left on the plate for a maximum period of 30 seconds. The response to the administration of the product is considered positive if at least a doubling of the normal reaction time is seen. The results obtained are given in Table 2 which records the

TABLE 1

Activity of proglumide in potentiating analgesia induced by opiates in the "Tail Flick" test

| Treatment | Dose mg/kg | 10' | 20' | 30' | 45' | 60' | 90' | $\overline{M}$ (1–90') ± S.E. | X |
|---|---|---|---|---|---|---|---|---|---|
| A | — | −10.2 ± 9.3 | 19.6 ± 4.1 | 46.4 ± 8.2 | −8.7 ± 13.5 | 18.2 ± 5.1 | 19.9 ± 8.3 | 14.2 ± 8.62 | — |
| B | 3 | 29.0 ± 20.4 | 35.0 ± 9.4 | 71.4 ± 12.1 | 49.3 ± 21.3 | 38.8 ± 23.9 | 38.3 ± 20.1 | 43.62 ± 7.37 | 1 |
| C | 1 + 3 (M) | 35.7 ± 19.6 | 50.8 ± 17.4 | 62.5 ± 16.6 | 89.5 ± 7.4 | 70.4 ± 20.1 | 13.0 ± 36.4 | 53.65 ± 26.9 | 1.23 |
| D | 5 + 3 (M) | 36.6 ± 16.2 | 28.1 ± 11.9 | 100.0 + 0 | 98.6 ± 1.4 | 75.5 ± 15.2 | 52.8 ± 25.1 | 75.27 ± 6.56 | 1.72 |
| E | 20 + 3 (M) | 68.9 ± 16.2 | 100.0 ± 0 | 95.2 + 4.8 | 81.8 ± 8.2 | 100.0 ± 0 | 100.0 ± 0 | 90.89 ± 5.27 | 2.08 |
| F | (D) 6 | 48.1 ± 18.8 | 32.9 ± 21.8 | 24.8 ± 28.0 | 50.6 ± 13.3 | 41.0 ± 20.5 | 3.5 ± 19.8 | 33.48 ± 7.16 | 1 |
| G | 1 + 6 (D) | 52.3 ± 12.6 | 73.7 ± 8.0 | 45.9 ± 7.7 | 31.6 ± 15.4 | 26.2 ± 11.8 | 22.8 ± 13.9 | 42.08 ± 7.86 | 1.26 |
| H | 5 + 6 (D) | 90.3 ± 9.7 | 94.6 ± 5.0 | 84.4 ± 9.1 | 39.7 ± 16.4 | 36.8 ± 5.2 | 29.8 ± 4.1 | 62.6 ± 12.3 | 1.86 |
| I | 20 + 6 (D) | 100.0 ± 0 | 97.2 ± 2.8 | 100.0 ± 0 | 97.7 ± 2.3 | 56.0 ± 18.7 | 25.5 ± 16.7 | 79.4 ± 12.85 | 2.37 |

N.B.: For each time the recorded values relate to groups of 5 animals.
Treatments:
A = Controls;
B = Morphine;
C = Proglumide + Morphine;
D = Proglumide + Morphine;
E = Proglumide + Morphine;
F = Dextropropoxyphene;
G = Proglumide + Dextropropoxyphene;
H = Proglumide + Dextropropoxyphene;
I = Proglumide + Dextropropoxyphene;
X = potency ratio with respect to morphine = 1

From the data given in Table 1, an ED50 value is calculated for potentiation of the analgesic effect induced by proglumide, or the quantity of proglumide in mg/kg capable of increasing the analgesic effect of the compound under consideration by 50%. ED50 values for the strengthening of morphine and propoxyphene respectively of 4.15 mg/kg and 2.26 mg/kg are thus obtained.

EXPERIMENT NO. 2

Hot plate test

The method is that described by Eddy et al. (J. Pharmac. Exp. Therm. 107, 385 (1953)).

Groups of five male rats having a weight of about 150 g and which have not been fasting are used.

groups treated, the doses administered and the stay times on the plate expressed as the number of positive responses over the number treated.

TABLE 2

Power of proglumide to potentiate the analgesic activity of opiates in the hot plate test.

| Treatment | Dosage mg/kg/sc | (positives/treated) Analgesic strengthening power in the plate test | | | | | | A* |
|---|---|---|---|---|---|---|---|---|
| | | 10' | 20' | 30' | 45' | 60' | 90' | |
| Morphine | 2.5 | 1/5 | 1/5 | 2/5 | 2/5 | 1/5 | 0/5 | 7 |
| Morphine + Proglumide | 2.5 + 1 (P) | 2/5 | 2/5 | 4/5 | 3/5 | 0/5 | 1/5 | 12 |
| Morphine + Proglumide | 2.5 + 5 (P) | 2/5 | 5/5 | 3/5 | 5/5 | 1/5 | 2/5 | 18 |
| Morphine + Proglumide | 2.5 + 20 (P) | 2/5 | 5/5 | 5/5 | 5/5 | 5/5 | 4/5 | 26 |
| Methadone | 1 | 1/5 | 2/5 | 1/5 | 2/5 | 1/5 | 1/5 | 8 |
| Methadone + Proglumide | 1 + 1 (P) | 0/5 | 2/5 | 2/5 | 3/5 | 0/5 | 1/5 | 8 |
| Methadone + Proglumide | 1 + 5 (P) | 3/5 | 4/5 | 4/5 | 2/5 | 3/5 | 0/5 | 16 |
| Methadone + Proglumide | 1 + 20 (P) | 4/5 | 5/5 | 5/5 | 4/5 | 5/5 | 4/5 | 27 |

Note:
A* = Tot. positive X/30

From the results given in the Table it may be seen that even 5 mg/kg s.c. doses or proglumide can at least double the analgesic effect of morphine and methadone.

EXPERIMENT NO. 3

Analgesic activity in the Randall-Selitto test

The method is that described by Winters et al (J. Pharmacol. Exp. Ther. 150, 165 (1965). Groups of five female rats having an average weight of about 100 g and which have not been fasting are used. A 20% saline solution of yeast is administered into the sub-plantar region of the right hind leg.

The compounds to be tested are administered s.c. 2 hours after the injection of inflammatory agent 0.5 hours after the administration of the drugs, the pain threshold is determined by measuring the pressure needed to induce a flight reaction in the animal. The results obtained are given in Table No. 3 which records the groups treated and the doses administered, the pain threshold expressed as a pressure exerted in mmHg to cause the pain stimulus (average±S.E.) and a statistical evaluation of the results of the various treated groups by the Student "t" test.

From the data given in Table No. 3, it is seen that, in all cases, 20 mg/kg of proglumide increases the analgesic effect of the narcotic 3 to 4 times in a significant manner.

Male rats having a weight of about 200 g, which have not been fasting, are used. The animals are stressed by the application to the front leg of a 60 Hz-2.5 mA current in pulses of a duration of one second every five seconds for 20 minutes.

This stress regime causes the release of endogenous opiates. Immediately after the electrical stimulation the animals are subjected to the Tail Flick Test at times indicated in the Table.

Proglumide is administered i.v. immediately before the electric shock at doses indicated in Table 4.

From the data given in Table 4 it is seen that, even at 5 mg/kg, proglumide can increase (in one case significantly) the analgesic effect of endogenous enkephalins while at 20 mg/kg the increase is significantly more marked both in intensity and duration.

TABLE NO. 3

Strengthening effect of proglumide on analgesia produced by opiates in the Randall-Selitto test.

| Treatment | Dose (mg/kg/sc) | Pain threshold (mmHg) M ± S.E. | t (vs controls) | Equivalent dose t (vs analgesic) |
|---|---|---|---|---|
| Controls | — | 12.5 ± 2.31 | — | — |
| Morphine | 0.5 | 22.0 ± 4.13 | 2.01 | — |
| Morphine | 2 | 51.4 ± 9.43** | 4.01 ($p < 0.01$) | — |
| Morphine + Proglumide | 0.5 + 5 (P) | 44.1 ± 13.75 | 2.27 | 1.53 (N.S.) |
| Morphine + Proglumide | 0.5 + 20 (P) | 62.1 ± 10.93** | 4.44 ($p < 0.01$) | 3.53 ($p < 0.01$) |
| Propoxyphene | 7.5 | 37.5 ± 7.12* | 3.34 ($p < 0.05$) | — |
| Propoxyphene | 25 | 50.7 ± 10.02** | 3.71 ($p < 0.01$) | — |
| Propoxyphene + Proglumide | 7.5 + 5 (P) | 45.6 ± 11.43* | 2.84 ($p < 0.05$) | 0.60 (N.S.) |
| Propoxyphene + Proglumide | 7.5 + 20 (P) | 64.8 ± 4.05*** | 11.02 ($p < 0.001$) | 3.33 ($p < 0.05$) |
| Pentazocine | 2 | 27.9 ± 5.71* | 2.50 ($p < 0.05$) | — |
| Pentazocine | 6 | 48.6 ± 4.93*** | 6.63 ($p < 0.001$) | — |
| Pentazocine + Proglumide | 2 + 5 (P) | 40.0 ± 7.61** | 3.46 ($p < 0.01$) | 1.27 (N.S.) |
| Pentazocine + Proglumide | 2 + 20 (P) | 59.2 ± 10.93*** | 4.18 ($p < 0.001$) | 2.54 ($p < 0.05$) |

EXPERIMENT NO. 4

Influence of proglumide on the analgesic activity of endogenous opiates released under transcutaneous shock in rats measured by the Tail Flick Test The method is that described by Lewis et al. (J. Naurosc. 1, 358 (1981)).

TABLE 4

Average latency (in sec) determined by the Tail Flick Test at different times (minutes) after the electric shock (average values for groups of animals ± S.E.)

| Treatment | Dose mg/kg/sc | 1' | 5' | 10' | 15' |
|---|---|---|---|---|---|
| Controls | — | 3.78 ± 0.21 | 4.01 ± 0.23 | 3.54 ± 0.19 | 3.83 ± 0.09 |
| Controls stress | | 6.93 ± 0.40 | 6.15 ± 0.39 | 4.36 ± 0.26 | 3.58 ± 0.17 |
| t (vs control) | | 6.91*** | 4.76** | 2.53* | 1.32 |
| Proglumide | 20 | 3.66 ± 0.25 | 3.59 ± 0.20 | 3.57 ± 0.16 | 3.57 ± 0.15 |
| t (vs control) | | 0.37 | 1.36 | 0.12 | 1.49 |
| t (vs control stress) | | 6.90*** | 5.88** | 2.57* | 0.04 |
| Stress + P | 1 | 6.37 ± 0.45 | 6.55 ± 0.43 | 4.07 ± 0.22 | 3.68 ± 0.16 |
| T (vs control) | | 5.21*** | 5.18*** | 1.83 | 0.82 |
| t (vs control stress) | | 0.92 | 0.69 | 0.86 | 0.43 |
| Stress + P | 5 | 6.33 ± 0.57 | 8.5 ± 0.76 | 4.66 ± 0.32 | 3.81 ± 0.16 |
| t (vs control) | | 4.25** | 5.62** | 2.98* | 0.11 |
| t (vs control | | 0.87 | 2.74* | 0.72 | 0.98 |

TABLE 4-continued

Average latency (in sec) determined by the Tail Flick Test at different times (minutes) after the electric shock (average values for groups of animals ± S.E.)

| Treatment | Dose mg/kg/sc | 1' | 5' | 10' | 15' |
|---|---|---|---|---|---|
| stress) | | | | | |
| Stress + P | 20 | 13.59 ± 1.0 | 9.16 ± 0.67 | 6.94 ± 0.44 | 4.78 ± 0.32 |
| t (vs control) | | 9.54*** | 7.29*** | 7.02*** | 2.89* |
| t (vs control stress) | | 6.14*** | 3.90** | 5.01*** | 3.34** |

*: ($p < 0.05$)
**: ($p < 0.01$)
***: ($p < 0.001$)

EXPERIMENT NO. 5

Activity of proglumide as an antagonist to the tolerance induced by opiates

Proglumide is capable of antagonising the development of tolerance induced by morphine.

Groups of five male rats having a weight of about 200–250 g were used.

At successive intervals of one hour each group received 10 mg/kg or morphine hydrochloride i.p.

The groups treated with proglumide also received quantities of proglumide at the doses indicated in Table 5 intraperitoneally, again at one hour intervals and administered immediately before the administration of morphine.

The determination of the pain threshold was effected 1, 3, 6, 9 and 12 hours after the first treatment by the Tail Flick test.

The data given in Table 5 indicate the percentage variations in the latency (appearance of pain) before and after treatment with the drugs.

From the data given in Table 5 it is seen that proglumide opposes the development of tolerance induced by the repeated administration of morphine. With a dose of 20 mg/kg this antagonism becomes highly significant.

Significant values (proglumide+morphine) towards morphine:

*: $P < 0.05$
**: $P < 0.01$

TABLE 5

Antagonism of proglumide to the development of tolerance in rats induced by the repeated administration of morphine HCl

| Treatment | Dose mg/kg i.p. | 1 h | 3 h | 6 h | 9 h | 12 h |
|---|---|---|---|---|---|---|
| Controls | (Saline) | 0.48 ± 9.82 | 29.7 ± 12.3 | 6.36 ± 12.9 | 1.18 ± 12.9 | 1.14 ± 11.2 |
| Morphine | 5 | 58.98 ± 16.3 | 67.58 ± 11.1 | 30.0 ± 15.3 | 38.62 ± 8.7 | 23.1 ± 8.6 |
| Morphine + Proglumide | 5 + 35 (P) | 72.96 ± 9.76 | 73.76 ± 10.70 | 68.62 ± 9.5 | 58.94 ± 4.5 | 53.74 ± 5.3 |
| Morphine + Proglumide | 5 + 20 (P) | 100 ± 0* | 92.4 ± 4.9 | 100 ± 0** | 90.5 ± 6.9** | 100 ± 0** |

TABLE 6

Increase in the analgesic effect of DALA induced by proglumide and determined by the Tail Flick tests on rats.

| Treatment | Doses µg/kg ICV | 5' | 15' | 30' | 45' | 60' | 90' | Average (0 → 90) | |
|---|---|---|---|---|---|---|---|---|---|
| A | — | 15.34 ± 11.6 | 13.62 ± 11.5 | 25.48 ± 9.6 | −1.68 ± 9.6 | −4.86 ± 11.3 | 0.8 ± 11.5 | 8.12 ± 4.84 | |
| B | 1 | 18.06 ± 10.8 | 2.18 ± 10.6 | 18.36 ± 5.9 | −10.94 ± 14.5 | −5.58 ± 8.1 | 13.3 ± 8.4 | 5.9 ± 5.12 | |
| C | 10 | 61.06 ± 11.8 | 51.04 ± 4.6 | 40.00 ± 9.04 | 25.24 ± 7.7 | 14.68 ± 9.2 | 10.06 ± 8.3 | 33.7 ± 8.3 | ↑ |
| D | 10 + 0.01 | 51.4 ± 9.4 | 61.08 ± 5.2 | 52.16 ± 10.5 | 35.7 ± 15.2 | 14.56 ± 12.3 | 24.5 ± 10.9 | 39.9 ± 7.4 | ↑↑ |
| E | 10 + 0.1 | 75.9 ± 10.8 | 97.68 ± 2.3 | 82.2 ± 8.3 | 60.24 ± 19.7 | 36.3 ± 11.4 | 14.38 ± 10.7 | 61.11 ± 12.6 | ↑↑ |
| F | 10 + 1 | 98.9 ± 1.1 | 100.0 ± 0 | 90.86 ± 5.7 | 62.36 ± 4.0 | 53.9 ± 10.3 | 16.78 ± 9.7 | 70.46 ± 13.3* | ↑↑ |

*: ($P$ 0.05) with respect to DALA group
↑: ($P$ 0.05) with respect to control group
↑↑: ($P$ 0.01) with respect to control group The values given in the table express the % variation in the latency to pain according to the formula explained above.
A: Controls
B: Proglumide
C: DALA
D: DALA + Proglumide
E: DALA + Proglumide
F: DALA + Proglumide

EXPERIMENT NO. 6

Potentiation of the analgesic activities of enkephalins induced by proglumide

In order to check one of the possible mechanisms for the action of proglumide, that is its possible inhibition of the enzymatic degradation of endogenous enkephalins, the following experiment was carried out:

A cannula was implanted in the right lateral ventricle of male rats having a weight of 150–200 g (groups of five animals were used) in order to allow the intracerebroventricular (I.C.V.) administration of drugs according to the method of Noble et al (Life Science 6, (1970) 281–291).

The animals were subsequently treated (I.C.V.) with 3 µg of D-ala-methionine-enkephalinamide (DALA) immediately after an injection (I.C.V.) of proglumide at the doses given in Table 6. Analgesia was tested for by the Tail Flick method already mentioned at the times given in the Table.

From the data given one can see the potentiating action of proglumide on the analgesic effect of the enkephalinamide (DALA) both in intensity and duration. This action, which is highly significant at doses of 1 μg/kg of proglumide, is clearly related to an inhibiting activity of proglumide on an enzyme (or enzymes) responsible for the metabolism of the enkephalins.

With reference to the synergic effect of proglumide on the analgesic activity of the opiate drugs examined, it was desired to test whether the therapeutic effect was also accompanied by synergism or by increase of toxicity.

The acute toxicity in female mice having an average weight of 20 g after fasting for 18 hours was thus determined.

The drug (or drugs) under examination was administered sub-cutaneously. The animals were kept under observation for 15 days after the administration.

Ten animals were used for each dose.

The acute toxicity of proglumide, morphine hydrochloride and methadone and any interaction between two drugs in a combination were thus determined according to the method proposed by Loewe et al (Arch. Exp. Path. Pharmak. 114, 3/3 (1962)).

The toxicities determined on groups of animals (10 animals/dose) are given by the ratios in Table 7.

The LD 50 was calculated according to the method described by Liechtfield & Wilcoxon (J. Pharmacol. Exp. Therap. 1949, 96).

TABLE 7

Determination of the acute toxicity s.c. of proglumide-morphine and proglumide-methadone pharmaceutical compositions.

| Proglumide/Analgesic relative ratios | LD 50 mg/kg s.c. | Quantities responsible for toxicity | |
|---|---|---|---|
| | | Proglumide | Analges. Narc. |
| 1:0 (Proglumide) | >5000 | — | — |
| 0.8:0.2 (P—morphine) | 2177.9 (1827–2596) | 1742.3 | 435.6 |
| 0.5:0.5 (P—morphine) | 866.8 (819–917) | 433.4 | 433.4 |
| 0.2:0.8 (P—morphine) | 589.4 (555–625) | 117.9 | 471.5 |
| 0:1 (morphine) | 458.3 (415–505) | — | 458.3 |
| 0.8:0.2 (P—methadone) | 287.9 (250–331) | 230.3 | 57.6 |
| 0.5:0.5 (P—methadone) | 121.8 (89–167) | 60.9 | 60.9 |
| 0.2:0.8 (P—methadone) | 71.4 (58–87) | 14.3 | 57.1 |
| 0:1 (methadone) | 53.5 (39.5–72.6) | — | 53.5 |

FIGS. 1 and 2 are graphs illustrating the theoretical and experimental interactions according to the data of Table 7 of the toxicity of the drugs making up the proglumide-morphine and proglumide-methadone combinations respectively. The graphs of FIGS. 1 and 2 give the quantity of proglumide in mg/kg s.c. on the abscissae and the quantity of morphine hydrochloride and methadone respectively in mg/kg s.c. on the ordinates.

In the graphs the expected straight-line correlation is indicated with A and the correlation of the experimental volumes is indicated with B.

The experimental results of Table 7 lie practically on the expected straight line for both combinations examined; one may thus conclude that there is no synergism or unexpected increase in the toxicity of the components in the pharmaceutical combinations studied which are the subject of the invention.

The experimental data given above appear to provide an extensive indication that the use of proglumide, either alone or in association with narcotic-analgesic drugs, is an innovation of considerable importance which can make available to the doctor a drug of pre-eminent therapeutic interest for the relief of pain of any etiology and intensity. Such treatment appears to be particularly indicated in the case of prolonged administrations when there is a very great need for the drug to be fully tolerated and not to cause habituation, or at least for this to be maintained within acceptable limits. Furthermore its possible use in the detoxication of patients made drug dependant by the prolonged use of opiate drugs appears to be of enormous therapeutic and social interest.

We claim:

1. A pharmaceutical composition for use in pain relief therapy in humans including proglumide or pharmaceutically-acceptable salt thereof and further including a drug selected from the group consisting of morphine and chemically related opioids, the amount of proglumide being effective to potentiate the analgesic-narcotic activity of said drug, wherein the ratio by weight of proglumide to the said drug is from about 200 to 1.

2. A pharmaceutical composition according to claim 1, wherein the drug having an analgesic-narcotic activity is selected from the group consisting of morphine, codeine, oxycodone, levorphanol, pentazocine, meperidine, dextropropoxyphene, pharmaceutically-acceptable salts thereof and mixtures thereof.

3. A pharmaceutical product comprising a drug selected from the group consisting of morphine and chemically related opioids and proglumide or one of its pharmaceutically-acceptable salts as a combined preparation for simultaneous, separate or sequential use in human pain relief therapy, wherein the ratio by weight of proglumide to the said drug is from about 200 to 1.

4. A method of treatment of pain condition in humans comprising administering proglumide or a pharmaceutically-acceptable salt thereof to a human suffering from said condition, wherein the proglumide or pharmaceutically-acceptable salt thereof is administered at a rate of 0.5–30 mg/kg of body weight.

5. A method according to claim 4, wherein proglumide or its pharmaceutically-acceptable salt is administered simultaneously, separately or sequentially with a drug selected from the group consisting of morphine and chemically related opioids, wherein the weight ratio of proglumide or pharmaceutically-acceptable salt thereof to the said drug is from about 200 to 1.

6. A method according to claim 5, wherein the analgesic-narcotic drug is selected from the group consisting of morphine, codeine, oxycodone, levorphanol, pentazocine, meperidine, methadone, dextropropoxyphene, pharmaceutically-acceptable salts thereof and mixtures thereof.

7. The method of claim 4 or 5 wherein the proglumide or pharmaceutically acceptable salt of proglumide, with an analgesic-narcotic drug, is administered orally, rectally or parenterally.

8. A method for potentiating the effect of endogenous enkephalins in a human comprising administering an effective amount of proglumide or its pharmaceutically acceptable salt to said human.

* * * * *